US006743907B1

(12) United States Patent
Donoho et al.

(10) Patent No.: US 6,743,907 B1
(45) Date of Patent: Jun. 1, 2004

(54) HUMAN PROTEINS AND POLYNUCLEOTIDES ENCODING THE SAME

(75) Inventors: Gregory Donoho, The Woodlands, TX (US); C. Alexander Turner, Jr., The Woodlands, TX (US); Michael C. Nehls, Stockdorf (DE); Glenn Friedrich, Houston, TX (US); Brian Zambrowicz, The Woodlands, TX (US); Arthur T. Sands, The Woodlands, TX (US)

(73) Assignee: Lexicon Genetics Incorporated, The Woodlands, TX (US)

( * ) Notice: Subject to any disclaimer, the term of this patent is extended or adjusted under 35 U.S.C. 154(b) by 0 days.

(21) Appl. No.: 09/691,344

(22) Filed: Oct. 18, 2000

Related U.S. Application Data

(60) Provisional application No. 60/160,285, filed on Oct. 19, 1999, and provisional application No. 60/183,583, filed on Feb. 18, 2000.

(51) Int. Cl.$^7$ .................. C07H 21/04; C07H 21/02; C07K 14/00

(52) U.S. Cl. .................. 536/23.5; 536/23.1; 536/24.1; 536/24.3; 530/350

(58) Field of Search .................. 536/23.1, 23.5, 536/24.1, 24.3; 530/350

(56) References Cited

U.S. PATENT DOCUMENTS

| | | | |
|---|---|---|---|
| 4,215,051 A | | 7/1980 | Schroeder et al. |
| 4,376,110 A | | 3/1983 | David et al. |
| 4,946,778 A | | 8/1990 | Ladner et al. |
| 5,837,458 A | | 11/1998 | Minshull et al. |
| 5,869,336 A | | 2/1999 | Meyer et al. |
| 5,877,397 A | | 3/1999 | Lonberg et al. |
| 6,075,181 A | | 6/2000 | Kucherlapati et al. |
| 6,242,419 B1 | * | 6/2001 | Strachan et al. .............. 514/12 |

OTHER PUBLICATIONS

Lander et al. "Human coagulation Factor V nucleotide sequence", Database: N_Geneseq_032802, Accession No.: AAZ32182; Jan. 13, 2000.*
Gijutsu et al. "Soluble neuropillin sNP–2 protein sequence", Database: A_Geneseq_032802, Accession No.: AAB24216; Feb. 6, 2001.*
Philips S, "Human DNA sequence from PAC 94G16 on chromosome 6q21," Database: NCBI, Locus: HS94G16, Accession No.: Z85999, Nov. 23, 1999.*
Y. Bidault, "The next generation of bioinformatics software: Examining proteins on the desktop computer", American Biotechnology Laboratory, Jan. 2002, p. 12.*
Mackay et al. "Human Tango 229 cDNA", Database: N_Geneseq_032802, Accession NO: AAS00660; Sep. 7, 2001.*
Mackay et al. "Human Tango 229 polypeptide", Database: A_Geneseq_032802, Accession NO: AAU00670; Sep. 7, 2001.*
Strachan et al. "Polynucleotide isolated from node stromal cells of fsn –/–mice", Feb. 19, 2001, Accession NO: AAA96736, Database: N_Geneseq_0328021.*
Bird et al, 1988, "Single–Chain Antigen–Binding Proteins", Science 242:423–426.
Bitter et al, 1987, "Expression and Secretion Vectors for Yeast", Methods in Enzymology 153:516–544.
Colbere–Garapin et al, 1981, "A New Dominant Hybrid Selective Marker for Higher Eukaryotic Cells", J. Mol. Biol. 150:1–14.
Gautier et al, 1987, "α–DNA IV:α–anomeric and β–anomeric tetrathymidylates covalently linked to interaclating oxazolopyridocarbazole. Synthesis, physiochemical properties and poly (rA) binding", Nucleic Acids Research 15(16):6625–6641.
Greenspan et al, 1993, "Idiotypes: structure and immunogenicity", FASEB Journal 7:437–444.
Huse et al, 1989, "Generation of a Large Combinatorial Library of the Immunglobulin Repertoire in Phage Lambda", Science 246:1275–1281.
Huston et al, 1988, "Protein engineering of antibody binding sites: Recovery of specific activity in an anti–digoxin single–chain Fv analogue produced in *Escherichia coli*", Proc. Natl. Acad. Sci. USA 85:5879–5883.
Inoue et al, 1987, "Sequence–dependent hydrolysis of RNA using modified oligonucleotide splints and R Nase H", FEBS Letters 215(2):327–330.
Inoue et al, 1987, "Synthesis and hybridization studies on two complementary nona(2'–O–methyl)ribonucleotides", Nucleic Acids Research 15(15):6131–6149.
Inouye & Inouye, 1985 "Up–promoter mutations in the lap gene of *Escherichia coli*", Nucleic Acids Research 13(9):3101–3110.
Janknecht et al, 1991, "Rapid and efficient purification of native histidine–tagged protein expressed by recombinant vaccinia virus", PNAS USA 88:8972–8976.
Kohler & Milstein, 1975, "Continuous cultures of fused cells secreting antibody of predefined specificity", Nature 256:495–497.
Logan et al., 1984, "Adenovirus tripartite leader sequence enhances translation of mRNAs late after infection", Proc. Natl. Acad. Sci. USA 81:3655–3659.
Lowry et al, 1980 "Isolation of Transforming DNA: Cloning the Hamster aprt Gene", Cell 22:817–823.
Morrison et al, 1984, "Chimeric human antibody molecules: Mouse antigen–binding domains with human constant region domains", Proc. Natl. Acad. Sci. USA 81:6851–6855.

(List continued on next page.)

*Primary Examiner*—Robert A. Wax
*Assistant Examiner*—Rita Mitra

(57) ABSTRACT

Novel human CUB domain containing protein polynucleotide and polypeptide sequences are disclosed that can be used in therapeutic, diagnostic, and pharmacogenomic applications.

5 Claims, No Drawings

OTHER PUBLICATIONS

Mulligan & Berg, 1981, "Selection for animal cells that express the *Escherichia coli* Gene Coding for xanthine–guanine phosphoribosyltransferase", Proc. Natl. Acad. Sci. USA 78(4):2072–2076.

Neuberger et al, 1984, "Recombinant antibodies possessing novel effector functions", Nature 312:604–608.

Nisonoff, 1991, "Idiotypes: Concepts and Application", J. of Immunology 147:2429–2438.

O'Hare et al, 1981, "Transformation of mouse fibroblasts to methotrexate resistance by a recombinant plasmid expressing a prokaryotic dihydrofolate reductase", Proc. Natl. Acad. Sci. USA 78(3):1527–1531.

Ruther et al, 1983, "Easy identification of cDNA clones", EMBO Journal 2(10):1791–1794.

Santerre et al, 1984, "Expression of prokaryotic genes for hygromycin B and G418 resistance as dominant–selection markers in mouse L cells", Gene 30:147–156.

Sarin et al, 1988, "Inhibition of acquired immunodeficiency syndrome virus by oligodeoxynucleoside methylphosphonates", Proc. Natl. Acad. Sci. USA 85:7448–7451.

Smith et al, 1983, "Molecular Engineering of the Autographa californica Nuclear Polyhedrosis Virus Genome: Deletion Mutations within the Polyherdrin Gene", J. Virol. 46(2):584–593.

Stein et al, 1988, "Physiochemical properties of phosphorothioate oligodeoxynucleotides", Nucleic Acids Research 16(8):3209–3221.

Szybalska & Szybalski, 1962, "Genetics of Human Cell Lines, IV DNA–Mediated Heritable Transformation of a Biochemical Trait", Proc. Natl. Acad. Sci. USA 48:2026–2034.

Takeda et al, 1985, "Construction of chimaeric processed immunoglobulin genes containing mouse variable and human constant region sequences", Nature 314:452–454.

Van Heeke et al, 1989, "Expression of Human Asparagine Synthetase in *Escherichia coli*", J. Biol. Chemistry 264(10):5503–5509.

Ward et al, 1989, "Binding activities of a repertoire of single immunoglobulin variable secreted from *Escherichia coli*", Nature 341:544–546.

Wigler et al, 1980, "Transformation of mammalian cells with an amplifiable dominant–acting gene", Proc. Natl. Acad. Sci. USA 77(6):3567–3570.

Wigler et al, 1977, "Transfer of Purified Herpes Virus Thymidine Kinase Gene to Cultured Mouse Cells", Cell 11:223–232.

* cited by examiner

SEQUENCE LISTING

<160> NUMBER OF SEQ ID NOS: 7

<210> SEQ ID NO 1
<211> LENGTH: 1464
<212> TYPE: DNA
<213> ORGANISM: homo sapiens

<400> SEQUENCE: 1

```
atgacatcta agaattatcc cgggacctac cccaatcaca ctgtttgcga aaagacaatt      60
acagtaccaa aggggaaaag actgattctg aggttgggag atttggatat cgaatcccag     120
acctgtgctt ctgactatct tctcttcacc agctcttcag atcaatatgg tccatactgt     180
ggaagtatga ctgttcccaa agaactcttg ttgaacacaa gtgaagtaac cgtccgcttt     240
gagagtggat cccacatttc tggccggggt tttttgctga cctatgcgag cagcgaccat     300
ccagatttaa taacatgttt ggaacgagct agccattatt tgaagacaga atacagcaaa     360
ttctgcccag ctggttgtag agacgtagca ggagacattt ctgggaatat ggtagatgga     420
tatagagata cctctttatt gtgcaaagct gccatccatg caggaataat tgctgatgaa     480
ctaggtggcc agatcagtgt gcttcagcgc aaagggatca gtcgatatga agggattctg     540
gccaatggtg ttctttcgag ggatggttcc ctgtcagaca agcgatttct gtttacctcc     600
aatggttgca gcagatcctt gagttttgaa cctgacgggc aaatcagagc ttcttcctca     660
tggcagtcgg tcaatgagag tggagaccaa gttcactggt ctcctggcca agcccgactt     720
caggaccaag gcccatcatg ggcttcgggc gacagtagca acaaccacaa accacgagag     780
tggctggaga tcgatttggg ggagaaaaag aaaataacag gaattaggac cacaggatct     840
acacagtcga acttcaactt ttatgttaag agttttgtga tgaacttcaa aaacaataat     900
tctaagtgga agacctataa aggaattgtg aataatgaag aaaaggtgtt tcagggtaac     960
tctaactttc gggacccagt gcaaacaat ttcatccctc ccatcgtggc cagatatgtg    1020
cgggttgtcc cccagacatg gcaccagagg atagccttga aggtggagct cattggttgc    1080
cagattacac aaggtaatga ttcattggtg tggcgcaaga caagtcaaag caccagtgtt    1140
tcaactaaga aagaagatga gacaatcaca aggcccatcc cctcggaaga aacatccaca    1200
ggaataaaca ttacaacggt ggctattcca ttggtgctcc ttgttgtcct ggtgtttgct    1260
ggaatgggga tctttgcagc ctttagaaag aagaagaaga aggaagtcc gtatggatca    1320
gcggaggctc agaaaacaga ctgttggaag cagattaaat atccctttgc cagacatcag    1380
tcagctgagt ttaccatcag ctatgataat gagaaggaga tgacacaaaa gttagatctc    1440
atcacaagtg atatggcagg ttaa                                           1464
```

<210> SEQ ID NO 2
<211> LENGTH: 487
<212> TYPE: PRT
<213> ORGANISM: homo sapiens -continued

```
<400> SEQUENCE: 2

Met Thr Ser Lys Asn Tyr Pro Gly Thr Tyr Pro Asn His Thr Val Cys
1               5                   10                  15

Glu Lys Thr Ile Thr Val Pro Lys Gly Lys Arg Leu Ile Leu Arg Leu
                20                  25                  30

Gly Asp Leu Asp Ile Glu Ser Gln Thr Cys Ala Ser Asp Tyr Leu Leu
            35                  40                  45

Phe Thr Ser Ser Ser Asp Gln Tyr Gly Pro Tyr Cys Gly Ser Met Thr
        50                  55                  60

Val Pro Lys Glu Leu Leu Asn Thr Ser Glu Val Thr Val Arg Phe
65                  70                  75                  80

Glu Ser Gly Ser His Ile Ser Gly Arg Gly Phe Leu Leu Thr Tyr Ala
                    85                  90                  95

Ser Ser Asp His Pro Asp Leu Ile Thr Cys Leu Glu Arg Ala Ser His
                100                 105                 110

Tyr Leu Lys Thr Glu Tyr Ser Lys Phe Cys Pro Ala Gly Cys Arg Asp
            115                 120                 125

Val Ala Gly Asp Ile Ser Gly Asn Met Val Asp Gly Tyr Arg Asp Thr
        130                 135                 140

Ser Leu Leu Cys Lys Ala Ala Ile His Ala Gly Ile Ile Ala Asp Glu
145                 150                 155                 160

Leu Gly Gly Gln Ile Ser Val Leu Gln Arg Lys Gly Ile Ser Arg Tyr
                    165                 170                 175

Glu Gly Ile Leu Ala Asn Gly Val Leu Ser Arg Asp Gly Ser Leu Ser
                180                 185                 190

Asp Lys Arg Phe Leu Phe Thr Ser Asn Gly Cys Ser Arg Ser Leu Ser
            195                 200                 205

Phe Glu Pro Asp Gly Gln Ile Arg Ala Ser Ser Ser Trp Gln Ser Val
        210                 215                 220

Asn Glu Ser Gly Asp Gln Val His Trp Ser Pro Gly Gln Ala Arg Leu
225                 230                 235                 240

Gln Asp Gln Gly Pro Ser Trp Ala Ser Gly Asp Ser Ser Asn Asn His
                    245                 250                 255

Lys Pro Arg Glu Trp Leu Glu Ile Asp Leu Gly Glu Lys Lys Lys Ile
                260                 265                 270

Thr Gly Ile Arg Thr Thr Gly Ser Thr Gln Ser Asn Phe Asn Phe Tyr
            275                 280                 285

Val Lys Ser Phe Val Met Asn Phe Lys Asn Asn Ser Lys Trp Lys
        290                 295                 300

Thr Tyr Lys Gly Ile Val Asn Glu Glu Lys Val Phe Gln Gly Asn
305                 310                 315                 320

Ser Asn Phe Arg Asp Pro Val Gln Asn Phe Ile Pro Pro Ile Val
                    325                 330                 335

Ala Arg Tyr Val Arg Val Pro Gln Thr Trp His Gln Arg Ile Ala
                340                 345                 350

Leu Lys Val Glu Leu Ile Gly Cys Gln Ile Thr Gln Gly Asn Asp Ser
            355                 360                 365

Leu Val Trp Arg Lys Thr Ser Gln Ser Thr Ser Val Ser Thr Lys Lys
        370                 375                 380

Glu Asp Glu Thr Ile Thr Arg Pro Ile Pro Ser Glu Glu Thr Ser Thr
385                 390                 395                 400

Gly Ile Asn Ile Thr Thr Val Ala Ile Pro Leu Val Leu Leu Val Val
                    405                 410                 415
```

```
Leu Val Phe Ala Gly Met Gly Ile Phe Ala Ala Phe Arg Lys Lys Lys
            420                 425                 430

Lys Lys Gly Ser Pro Tyr Gly Ser Ala Glu Ala Gln Lys Thr Asp Cys
        435                 440                 445

Trp Lys Gln Ile Lys Tyr Pro Phe Ala Arg His Gln Ser Ala Glu Phe
    450                 455                 460

Thr Ile Ser Tyr Asp Asn Glu Lys Glu Met Thr Gln Lys Leu Asp Leu
465                 470                 475                 480

Ile Thr Ser Asp Met Ala Gly
                485

<210> SEQ ID NO 3
<211> LENGTH: 1761
<212> TYPE: DNA
<213> ORGANISM: homo sapiens

<400> SEQUENCE: 3
atgggattcg gtgcgggca gcgactgcgc cccgtcccgg cgccgcgctc gtccgcagag      60
gaggcggccc ggcccgggca gctgcggctc gggatccgtc gagggaggc cgagcttgcc    120 aagctggcgc ccagcggggt catggtgccc ggcgcccgcg gcggcggcgc actggcgcgg    180
gctgccgggc ggggcctcct ggctttgctg ctcgcggtct ccgccccgct ccggctgcag    240
gcggaggagc tgggtgatgg ctgtggacac tagtgactt atcaggatag tggcacaatg    300
acatctaaga attatcccgg gacctacccc aatcacactg tttgcgaaaa gacaattaca    360
gtaccaaagg ggaaaagact gattctgagg ttgggagatt tggatatcga atcccagacc    420
tgtgcttctg actatcttct cttccaccagc tcttcagatc aatatggtcc atactgtgga    480
agtatgactg ttcccaaaga actcttgttg aacacaagtg aagtaaccgt ccgctttgag    540
agtggatccc acatttctgg ccgggttttt ttgctgacct atgcgagcag cgaccatcca    600
gatttaataa catgtttgga acgagctagc cattatttga agacagaata cagcaaattc    660
tgcccagctg gttgtagaga cgtagcagga gacatttctg gaatatggt agatggatat    720 agagatacct ctttattgtg caaagctgcc atccatgcag aataattgc tgatgaacta    780 ggtggccaga tcagtgtgct tcagcgcaaa gggatcagtc gatatgaagg gattctggcc    840
aatggtgttc tttcgaggga tggttccctg tcagacaagc gatttctgtt tacctccaat    900
ggttgcagca gatccttgag ttttgaacct gacgggcaaa tcagagcttc ttcctcatgg    960
cagtcggtca tgagagtgg agaccaagtt cactggtctc ctggccaagc ccgacttcag   1020
gaccaaggcc atcatgggc ttcgggcgac agtagcaaca accacaaacc acgagagtgg   1080
ctggagatcg atttggggga gaaaagaaa ataacaggaa ttaggaccac aggatctaca   1140
cagtcgaact tcaaccttta tgttaagagt tttgtgatga acttcaaaaa caataattct   1200
aagtggaaga cctataaagg aattgtgaat aatgaagaaa aggtgtttca gggtaactct   1260
aactttcggg acccagtgca aaacaatttc atccctccca tcgtggccag atatgtgcgg   1320
gttgtccccc agacatggca ccagaggata gccttgaagg tggagctcat ggttgccag    1380 attacacaag gtaatgattc attggtgtgg cgcaagacaa gtcaaagcac cagtgttca    1440 actaagaaag aagatgagac aatcacaagg cccatcccct cggaagaaac atccacagga   1500
ataaacatta caacggtggc tattccatg gtgctccttg ttgtcctggt gtttgctgga   1560
atggggatct ttgcagcctt tagaaagaag aagaagaaag gaagtccgta tggatcagcg   1620
gaggctcaga aaacagactg ttggaagcag attaaatatc cctttgccag acatcagtca   1680
```

-continued

```
gctgagttta ccatcagcta tgataatgag aaggagatga cacaaaagtt agatctcatc    1740
acaagtgata tggcaggtta a                                              1761
```

<210> SEQ ID NO 4
<211> LENGTH: 586
<212> TYPE: PRT
<213> ORGANISM: homo sapiens

<400> SEQUENCE: 4

```
Met Gly Phe Gly Ala Gly Gln Arg Leu Arg Pro Val Pro Ala Pro Arg
 1               5                  10                  15

Ser Ser Ala Glu Glu Ala Ala Arg Pro Gly Gln Leu Arg Leu Gly Ile
            20                  25                  30

Arg Arg Gly Glu Ala Glu Leu Ala Lys Leu Ala Pro Ser Gly Val Met
        35                  40                  45

Val Pro Gly Ala Arg Gly Gly Ala Leu Ala Arg Ala Ala Gly Arg
    50                  55                  60

Gly Leu Leu Ala Leu Leu Leu Ala Val Ser Ala Pro Leu Arg Leu Gln
65                  70                  75                  80

Ala Glu Glu Leu Gly Asp Gly Cys Gly His Leu Val Thr Tyr Gln Asp
                85                  90                  95

Ser Gly Thr Met Thr Ser Lys Asn Tyr Pro Gly Thr Tyr Pro Asn His
            100                 105                 110

Thr Val Cys Glu Lys Thr Ile Thr Val Pro Lys Gly Lys Arg Leu Ile
        115                 120                 125

Leu Arg Leu Gly Asp Leu Asp Ile Glu Ser Gln Thr Cys Ala Ser Asp
    130                 135                 140

Tyr Leu Leu Phe Thr Ser Ser Asp Gln Tyr Gly Pro Tyr Cys Gly
145                 150                 155                 160

Ser Met Thr Val Pro Lys Glu Leu Leu Leu Asn Thr Ser Glu Val Thr
                165                 170                 175

Val Arg Phe Glu Ser Gly Ser His Ile Ser Gly Arg Gly Phe Leu Leu
            180                 185                 190

Thr Tyr Ala Ser Ser Asp His Pro Asp Leu Ile Thr Cys Leu Glu Arg
        195                 200                 205

Ala Ser His Tyr Leu Lys Thr Glu Tyr Ser Lys Phe Cys Pro Ala Gly
    210                 215                 220

Cys Arg Asp Val Ala Gly Asp Ile Ser Gly Asn Met Val Asp Gly Tyr
225                 230                 235                 240

Arg Asp Thr Ser Leu Leu Cys Lys Ala Ala Ile His Ala Gly Ile Ile
                245                 250                 255

Ala Asp Glu Leu Gly Gly Gln Ile Ser Val Leu Gln Arg Lys Gly Ile
            260                 265                 270

Ser Arg Tyr Glu Gly Ile Leu Ala Asn Gly Val Leu Ser Arg Asp Gly
        275                 280                 285

Ser Leu Ser Asp Lys Arg Phe Leu Phe Thr Ser Asn Gly Cys Ser Arg
    290                 295                 300

Ser Leu Ser Phe Glu Pro Asp Gly Gln Ile Arg Ala Ser Ser Ser Trp
305                 310                 315                 320

Gln Ser Val Asn Glu Ser Gly Asp Gln Val His Trp Ser Pro Gly Gln
                325                 330                 335

Ala Arg Leu Gln Asp Gln Gly Pro Ser Trp Ala Ser Gly Asp Ser Ser
            340                 345                 350
```

```
Asn Asn His Lys Pro Arg Glu Trp Leu Glu Ile Asp Leu Gly Glu Lys
            355                 360                 365

Lys Lys Ile Thr Gly Ile Arg Thr Thr Gly Ser Thr Gln Ser Asn Phe
        370                 375                 380

Asn Phe Tyr Val Lys Ser Phe Val Met Asn Phe Lys Asn Asn Asn Ser
385                 390                 395                 400

Lys Trp Lys Thr Tyr Lys Gly Ile Val Asn Asn Glu Glu Lys Val Phe
            405                 410                 415

Gln Gly Asn Ser Asn Phe Arg Asp Pro Val Gln Asn Asn Phe Ile Pro
        420                 425                 430

Pro Ile Val Ala Arg Tyr Val Arg Val Pro Gln Thr Trp His Gln
            435                 440                 445

Arg Ile Ala Leu Lys Val Glu Leu Ile Gly Cys Gln Ile Thr Gln Gly
        450                 455                 460

Asn Asp Ser Leu Val Trp Arg Lys Thr Ser Gln Ser Thr Ser Val Ser
465                 470                 475                 480

Thr Lys Lys Glu Asp Glu Thr Ile Thr Arg Pro Ile Pro Ser Glu Glu
            485                 490                 495

Thr Ser Thr Gly Ile Asn Ile Thr Thr Val Ala Ile Pro Leu Val Leu
        500                 505                 510

Leu Val Val Leu Val Phe Ala Gly Met Gly Ile Phe Ala Ala Phe Arg
            515                 520                 525

Lys Lys Lys Lys Lys Gly Ser Pro Tyr Gly Ser Ala Glu Ala Gln Lys
        530                 535                 540

Thr Asp Cys Trp Lys Gln Ile Lys Tyr Pro Phe Ala Arg His Gln Ser
545                 550                 555                 560

Ala Glu Phe Thr Ile Ser Tyr Asp Asn Glu Lys Glu Met Thr Gln Lys
            565                 570                 575

Leu Asp Leu Ile Thr Ser Asp Met Ala Gly
        580                 585

<210> SEQ ID NO 5
<211> LENGTH: 1620
<212> TYPE: DNA
<213> ORGANISM: homo sapiens

<400> SEQUENCE: 5
atggtgcccg cgcccgcgg cggcggcgca ctggcgcggg ctgccgggcg gggcctcctg      60
gctttgctgc tcgcggtctc cgccccgctc cggctgcagg cggaggagct gggtgatggc    120
tgtggacacc tagtgactta tcaggatagt ggcacaatga catctaagaa ttatcccggg    180
acctacccca tcacactgt ttgcgaaaag acaattacag taccaaaggg gaaaagactg    240
attctgaggt tgggagattt ggatatcgaa tcccagacct gtgcttctga ctatcttctc    300
ttcaccagct cttcagatca atatggtcca tactgtggaa gtatgactgt tcccaaagaa    360
ctcttgttga acacaagtga agtaaccgtc cgctttgaga gtggatccca catttctggc    420
cggggttttt tgctgaccta tgcgagcagc gaccatccag atttaataac atgtttggaa    480
cgagctagcc attatttgaa gacagaatac agcaaattct gcccagctgg ttgtagagac    540
gtagcaggag acatttctgg gaatatggta gatggatata gagataccct tttattgtgc    600
aaagctgcca tccatgcagg aataattgct gatgaactag gtggccagat cagtgtgctt    660
cagcgcaaag ggatcagtcg atatgaaggg attctggcca atggtgttct ttcgagggat    720
ggttccctgt cagacaagcg atttctgttt acctccaatg gttgcagcag atccttgagt    780
```

-continued

```
tttgaacctg acgggcaaat cagagcttct tcctcatggc agtcggtcaa tgagagtgga    840
gaccaagttc actggtctcc tggccaagcc cgacttcagg accaaggccc atcatgggct    900
tcgggcgaca gtagcaacaa ccacaaacca cgagagtggc tggagatcga tttgggggag    960
aaaaagaaaa taacaggaat taggaccaca ggatctacac agtcgaactt caacttttat   1020
gttaagagtt ttgtgatgaa cttcaaaaac aataattcta agtggaagac ctataaagga   1080
attgtgaata atgaagaaaa ggtgtttcag ggtaactcta actttcggga cccagtgcaa   1140
aacaatttca tccctcccat cgtggccaga tatgtgcggg ttgtccccca gacatggcac   1200
cagaggatag ccttgaaggt ggagctcatt ggttgccaga ttacacaagg taatgattca   1260
ttggtgtggc gcaagacaag tcaaagcacc agtgtttcaa ctaagaaaga agatgagaca   1320
atcacaaggc ccatcccctc ggaagaaaca tccacaggaa taaacattac aacggtggct   1380
attccattgg tgctccttgt tgtcctggtg tttgctggaa tggggatctt tgcagccttt   1440
agaaagaaga agaagaaagg aagtccgtat ggatcagcgg aggctcagaa acagactgt   1500
tggaagcaga ttaaatatcc ctttgccaga catcagtcag ctgagtttac catcagctat   1560
gataatgaga aggagatgac acaaaagtta gatctcatca caagtgatat ggcaggttaa   1620
```

<210> SEQ ID NO 6
<211> LENGTH: 539
<212> TYPE: PRT
<213> ORGANISM: homo sapiens

<400> SEQUENCE: 6

```
Met Val Pro Gly Ala Arg Gly Gly Ala Leu Ala Arg Ala Gly
 1               5                  10                  15

Arg Gly Leu Leu Ala Leu Leu Leu Ala Val Ser Ala Pro Leu Arg Leu
                 20                  25                  30

Gln Ala Glu Glu Leu Gly Asp Gly Cys Gly His Leu Val Thr Tyr Gln
             35                  40                  45

Asp Ser Gly Thr Met Thr Ser Lys Asn Tyr Pro Gly Thr Tyr Pro Asn
         50                  55                  60

His Thr Val Cys Glu Lys Thr Ile Thr Val Pro Lys Gly Lys Arg Leu
 65                  70                  75                  80

Ile Leu Arg Leu Gly Asp Leu Asp Ile Glu Ser Gln Thr Cys Ala Ser
                 85                  90                  95

Asp Tyr Leu Leu Phe Thr Ser Ser Asp Gln Tyr Gly Pro Tyr Cys
             100                 105                 110

Gly Ser Met Thr Val Pro Lys Glu Leu Leu Leu Asn Thr Ser Glu Val
             115                 120                 125

Thr Val Arg Phe Glu Ser Gly Ser His Ile Ser Gly Arg Gly Phe Leu
         130                 135                 140

Leu Thr Tyr Ala Ser Ser Asp His Pro Asp Leu Ile Thr Cys Leu Glu
145                 150                 155                 160

Arg Ala Ser His Tyr Leu Lys Thr Glu Tyr Ser Lys Phe Cys Pro Ala
                 165                 170                 175

Gly Cys Arg Asp Val Ala Gly Asp Ile Ser Gly Asn Met Val Asp Gly
             180                 185                 190

Tyr Arg Asp Thr Ser Leu Leu Cys Lys Ala Ala Ile His Ala Gly Ile
         195                 200                 205

Ile Ala Asp Glu Leu Gly Gly Gln Ile Ser Val Leu Gln Arg Lys Gly
     210                 215                 220

Ile Ser Arg Tyr Glu Gly Ile Leu Ala Asn Gly Val Leu Ser Arg Asp
```

```
                    225                 230                 235                 240
Gly Ser Leu Ser Asp Lys Arg Phe Leu Phe Thr Ser Asn Gly Cys Ser
                245                 250                 255
Arg Ser Leu Ser Phe Glu Pro Asp Gly Gln Ile Arg Ala Ser Ser Ser
                260                 265                 270
Trp Gln Ser Val Asn Glu Ser Gly Asp Gln Val His Trp Ser Pro Gly
            275                 280                 285
Gln Ala Arg Leu Gln Asp Gln Gly Pro Ser Trp Ala Ser Gly Asp Ser
        290                 295                 300
Ser Asn Asn His Lys Pro Arg Glu Trp Leu Glu Ile Asp Leu Gly Glu
305                 310                 315                 320
Lys Lys Lys Ile Thr Gly Ile Arg Thr Thr Gly Ser Thr Gln Ser Asn
                325                 330                 335
Phe Asn Phe Tyr Val Lys Ser Phe Val Met Asn Phe Lys Asn Asn Asn
                340                 345                 350
Ser Lys Trp Lys Thr Tyr Lys Gly Ile Val Asn Asn Glu Glu Lys Val
            355                 360                 365
Phe Gln Gly Asn Ser Asn Phe Arg Asp Pro Val Gln Asn Asn Phe Ile
        370                 375                 380
Pro Pro Ile Val Ala Arg Tyr Val Arg Val Pro Gln Thr Trp His
385                 390                 395                 400
Gln Arg Ile Ala Leu Lys Val Glu Leu Ile Gly Cys Gln Ile Thr Gln
                405                 410                 415
Gly Asn Asp Ser Leu Val Trp Arg Lys Thr Ser Gln Ser Thr Ser Val
            420                 425                 430
Ser Thr Lys Lys Glu Asp Glu Thr Ile Thr Arg Pro Ile Pro Ser Glu
        435                 440                 445
Glu Thr Ser Thr Gly Ile Asn Ile Thr Thr Val Ala Ile Pro Leu Val
    450                 455                 460
Leu Leu Val Val Leu Val Phe Ala Gly Met Gly Ile Phe Ala Ala Phe
465                 470                 475                 480
Arg Lys Lys Lys Lys Gly Ser Pro Tyr Gly Ser Ala Glu Ala Gln
                485                 490                 495
Lys Thr Asp Cys Trp Lys Gln Ile Lys Tyr Pro Phe Ala Arg His Gln
            500                 505                 510
Ser Ala Glu Phe Thr Ile Ser Tyr Asp Asn Glu Lys Glu Met Thr Gln
        515                 520                 525
Lys Leu Asp Leu Ile Thr Ser Asp Met Ala Gly
    530                 535
```

<210> SEQ ID NO 7
<211> LENGTH: 1768
<212> TYPE: DNA
<213> ORGANISM: homo sapiens

<400> SEQUENCE: 7

```
ggcggaggag ctgggtgatg gctgtggaca cctagtgact tatcaggata gtggcacaat     60
gacatctaag aattatcccg ggacctaccc caatcacact gtttgcgaaa agacaattac    120
agtaccaaag gggaaaagac tgattctgag gttgggagat tggatatcg  atcccagac    180
ctgtgcttct gactatcttc tcttcaccag ctcttcagat caatatggtc catactgtgg    240
aagtatgact gttcccaaag aactcttgtt gaacacaagt gaagtaaccg tccgctttga    300
gagtggatcc cacatttctg ccgggggttt tttgctgacc tatgcgagca gcgaccatcc    360
```

-continued

```
agatttaata acatgtttgg aacgagctag ccattatttg aagacagaat acagcaaatt    420
ctgcccagct ggttgtagag acgtagcagg agacatttct gggaatatgg tagatggata    480
tagagatacc tctttattgt gcaaagctgc catccatgca ggaataattg ctgatgaact    540
aggtggccag atcagtgtgc ttcagcgcaa agggatcagt cgatatgaag ggattctggc    600
caatggtgtt ctttcgaggg atggttccct gtcagacaag cgatttctgt ttacctccaa    660
tggttgcagc agatccttga gttttgaacc tgacgggcaa atcagagctt cttcctcatg    720
gcagtcggtc aatgagagtg gagaccaagt tcactggtct cctggccaag cccgacttca    780
ggaccaaggc ccatcatggg cttcgggcga cagtagcaac aaccacaaac cacgagagtg    840
gctggagatc gatttggggg agaaaaagaa aataacagga attaggacca caggatctac    900
acagtcgaac ttcaactttt atgttaagag ttttgtgatg aacttcaaaa acaataattc    960
taagtggaag acctataaag gaattgtgaa taatgaagaa aaggtgtttc agggtaactc   1020
taactttcgg gacccagtgc aaaacaattt catccctccc atcgtggcca gatatgtgcg   1080
ggttgtcccc cagacatggc accagaggat agccttgaag gtggagctca ttggttgcca   1140
gattacacaa ggtaatgatt cattggtgtg gcgcaagaca agtcaaagca ccagtgtttc   1200
aactaagaaa gaagatgaga caatcacaag gcccatcccc tcggaagaaa catccacagg   1260
aataaacatt acaacggtgg ctattccatt ggtgctcctt gttgtcctgg tgtttgctgg   1320 aatgggatc tttgcagcct ttagaaagaa gaagaagaaa ggaagtccgt atggatcagc   1380
ggaggctcag aaaacagact gttggaagca gattaaatat ccctttgcca gacatcagtc   1440
agctgagttt accatcagct atgataatga gaaggagatg acacaaaagt tagatctcat   1500
cacaagtgat atggcaggtt aactccgttg actgccaaaa tagcatcccc aacgtgcagc   1560
cctccgcatc tatcagcagg ttgccccgga tggatctcag agatgaggat tggaacacca   1620
tgttctttcc caccctaaca acaacaaagg gcagtaaatt aaagtactct ttgtaaggta   1680
cagttaccga ttaatctaga gataaaatat tttcttaaaa atatatttca ttaaacacct   1740
atgctgtctc tatgcaaaaa aaaaaaaa                                     1768
```

HUMAN PROTEINS AND POLYNUCLEOTIDES ENCODING THE SAME

The present invention claims the benefit of U.S. Provisional Application No. 60/160,285 and 60/183,583 which were filed Oct. 19, 1999 and Feb. 18, 2000 respectively and are herein incorporated in their entirety.

1. INTRODUCTION

The present invention relates to the discovery, identification, and characterization of novel human polynucleotides encoding proteins sharing sequence similarity with mammalian proteins having CUB domains. The invention encompasses the described polynucleotides, host cell expression systems, the encoded proteins, fusion proteins, polypeptides and peptides, antibodies to the encoded proteins and peptides, and genetically engineered animals that either lack or over express the disclosed sequences, antagonists and agonists of the proteins, and other compounds that modulate the expression or activity of the proteins encoded by the disclosed polynucleotides that can be used for diagnosis, drug screening, clinical trial monitoring, or the treatment of physiological disorders, or diseases.

2. BACKGROUND OF THE INVENTION

The CUB domain is an extracellular domain (ECD) present in variety of diverse proteins such as bone morphogenetic protein 1, proteinases, spermadhesins, complement subcomponents, and neuronal recognition molecules. Given the importance of these functions, CUB proteins have been associated with, inter alia, regulating development, modulating cellular processes, and preventing infectious disease.

3. SUMMARY OF THE INVENTION

The present invention relates to the discovery, identification, and characterization of nucleotides that encode novel human proteins, and the corresponding amino acid sequences of these proteins. The novel human proteins (NHPs) described for the first time herein share structural similarity with animal CUB domain proteins, coagulation factors V and XIII, milk fat globule-EGF factor 8, transcriptional repressor AE-binding protein-1, and neuropilins 1 and 2 (which, like the presently described protein, contain both CUB and discoidin domains).

The novel human nucleic acid (cDNA) sequences described herein, encode proteins/open reading frames (ORFs) of 487, 586, and 539 amino acids in length (see SEQ ID NOS: 2, 4, and 6 respectively).

The invention also encompasses agonists and antagonists of the described NHPs, including small molecules, large molecules, mutant NHPs, or portions thereof that compete with native NHPs, NHP peptides, and antibodies, as well as nucleotide sequences that can be used to inhibit the expression of the described NHPs (e.g., antisense and ribozyme molecules, and gene or regulatory sequence replacement constructs) or to enhance the expression of the described NHPs (e.g., expression constructs that place the described gene under the control of a strong promoter system), and transgenic animals that express a NHP transgene, or "knockouts" (which can be conditional) that do not express a functional NHP. Several knockout ES cell lines have been produced that contain a gene trap mutation in a murine ortholog/homolog of the disclosed NHPs.

Further, the present invention also relates to processes for identifying compounds that modulate, i.e., act as agonists or antagonists, of NHP expression and/or NHP activity that utilize purified preparations of the described NHPs and/or NHP products, or cells expressing the same. Such compounds can be used as therapeutic agents for the treatment of any of a wide variety of symptoms associated with biological disorders or imbalances.

4. DESCRIPTION OF THE SEQUENCE LISTING AND FIGURES

The Sequence Listing provides the sequences of several NHP ORFs encoding the described NHP amino acid sequences. SEQ ID NO:7 describes a NHP ORF and flanking sequences.

5. DETAILED DESCRIPTION OF THE INVENTION

The NHPs described for the first time herein are novel proteins that are expressed in, inter alia, human cell lines, and human prostate, pituitary, fetal brain, brain, thymus, spleen, lymph node, trachea, kidney, fetal liver, thyroid, adrenal gland, salivary gland, stomach, small intestine, colon, muscle, heart, mammary gland, adipose, skin, esophagus, bladder, cervix, rectum, and testis cells.

The described sequences were compiled from gene trapped cDNAs, genomic sequence, and clones isolated from human brain, adipose, testis, and placenta cDNA libraries (Edge Biosystems, Gaithersburg, Md., and Clontech, Palo Alto, Calif.). The present invention encompasses the nucleotides presented in the Sequence Listing, host cells expressing such nucleotides, the expression products of such nucleotides, and: (a) nucleotides that encode mammalian homologs of the described genes, including the specifically described NHPs, and NHP products; (b) nucleotides that encode one or more portions of a NHP that correspond to functional domains, and the polypeptide products specified by such nucleotide sequences, including but not limited to the novel regions of any active domain(s); (c) isolated nucleotides that encode mutant versions, engineered or naturally occurring, of the described NHPs in which all or a part of at least one domain is deleted or altered, and the polypeptide products specified by such nucleotide sequences, including but not limited to soluble proteins and peptides in which all or a portion of the signal sequence is deleted; (d) nucleotides that encode chimeric fusion proteins containing all or a portion of a coding region of a NHP, or one of its domains (e.g., a receptor or ligand binding domain, accessory protein/self-association domain, etc.) fused to another peptide or polypeptide; or (e) therapeutic or diagnostic derivatives of the described polynucleotides such as oligonucleotides, antisense polynucleotides, ribozymes, dsRNA, or gene therapy constructs comprising a sequence first disclosed in the Sequence Listing.

As discussed above, the present invention includes: (a) the human DNA sequences presented in the Sequence Listing (and vectors comprising the same) and additionally contemplates any nucleotide sequence encoding a contiguous NHP open reading frame (ORF), or a contiguous exon splice junction first described in the Sequence Listing, that hybridizes to a complement of a DNA sequence presented in the Sequence Listing under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1 % SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encodes a functionally equivalent gene product. Additionally contemplated are any nucleotide sequences that hybridize to the complement of the DNA sequence that encode and express an amino acid sequence presented in the Sequence Listing under moderately stringent conditions, e.g., washing in 0.2×SSC/0.1 % SDS at 42° C. (Ausubel et al., 1989, supra), yet still encode a functionally equivalent NHP product. Functional equivalents of a NHP include naturally occurring NHPs present in other species and mutant NHPs whether naturally occurring or engineered (by site directed mutagenesis, gene shuffling, directed evolution as described in, for example, U.S. Pat. No. 5,837,458). The invention also includes degenerate nucleic acid variants of the disclosed NHP polynucleotide sequences.

Additionally contemplated are polynucleotides encoding a NHP ORF, or its functional equivalent, encoded by a polynucleotide sequence that is about 99, 95, 90, or about 85 percent similar or identical to corresponding regions of the nucleotide sequences of the Sequence Listing (as measured by BLAST sequence comparison analysis using, for example, the GCG sequence analysis package using standard default settings).

The invention also includes nucleic acid molecules, preferably DNA molecules, that hybridize to, and are therefore the complements of, the described NHP gene nucleotide sequences. Such hybridization conditions may be highly stringent or less highly stringent, as described above. In instances where the nucleic acid molecules are deoxyoligonucleotides ("DNA oligos"), such molecules are generally about 16 to about 100 bases long, or about 20 to about 80, or about 34 to about 45 bases long, or any variation or combination of sizes represented therein that incorporate a contiguous region of sequence first disclosed in the Sequence Listing. Such oligonucleotides can be used in conjunction with the polymerase chain reaction (PCR) to screen libraries, isolate clones, and prepare cloning and sequencing templates, etc.

Alternatively, such NHP oligonucleotides can be used as hybridization probes for screening libraries, and assessing gene expression patterns (particularly using a micro array or high-throughput "chip" format). Additionally, a series of the described NHP oligonucleotide sequences, or the complements thereof, can be used to represent all or a portion of the described NHP sequences. The oligonucleotides, typically between about 16 to about 40 (or any whole number within the stated range) nucleotides in length may partially overlap each other and/or a NHP sequence may be represented using oligonucleotides that do not overlap. Accordingly, the described NHP polynucleotide sequences shall typically comprise at least about two or three distinct oligonucleotide sequences of at least about 18, and preferably about 25, nucleotides in length that are each first disclosed in the described Sequence Listing. Such oligonucleotide sequences may begin at any nucleotide present within a sequence in the Sequence Listing and proceed in either a sense (5'-to-3') orientation vis-a-vis the described sequence or in an antisense orientation.

For oligonucleotide probes, highly stringent conditions may refer,. e.g., to washing in 6×SSC/0.05 % sodium pyrophosphate at 37° C. (for 14-base oligos), 48° C. (for 17-base oligos), 55° C. (for 20-base oligos), and 60° C. (for 23-base oligos). These nucleic acid molecules may encode or act as NHP gene antisense molecules, useful, for example, in NHP gene regulation (for and/or as antisense primers in amplification reactions of NHP gene nucleic acid sequences). With respect to NHP gene regulation, such techniques can be used to regulate biological functions. Further, such sequences may be used as part of ribozyme and/or triple helix sequences that are also useful for NHP gene regulation.

Inhibitory antisense or double stranded oligonucleotides can additionally comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide can also comprise at least one modified sugar moiety selected from the group including but not limited to arabinose, 2-fluoroarabinose, xylulose, and hexose.

In yet another embodiment, the antisense oligonucleotide will comprise at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-0-methylribonucleotide (Inoue et al., 1987, Nucl. Acids Res.15:6131–6148), or a chimeric RNA-DNA analogue (Inoue et al., 1987, FEBS Lett. 215:327–330). Alternatively, double stranded RNA can be used to disrupt the expression and function of a targeted NHP.

Oligonucleotides of the invention can be synthesized by standard methods known in the art, e.g. by use of an automated DNA synthesizer (such as are commercially available from Biosearch, Applied Biosystems, etc.). As examples, phosphorothioate oligonucleotides can be synthesized by the method of Stein et al. (1988, Nucl. Acids Res. 16:3209), and methylphosphonate oligonucleotides can be prepared by use of controlled pore glass polymer supports (Sarin et al., 1988, Proc. Natl. Acad. Sci. U.S.A. 85:7448–7451), etc.

Low stringency conditions are well known to those of skill in the art, and will vary predictably depending on the specific organisms, from which the library and the labeled sequences are derived. For guidance regarding such conditions see, for example, Sambrook et al., 1989, Molecular Cloning, A Laboratory Manual (and periodic updates thereof), Cold Springs Harbor Press, N.Y.; and Ausubel et al., 1989, Current Protocols in Molecular Biology, Green Publishing Associates and Wiley Interscience, N.Y.

Alternatively, suitably labeled NHP nucleotide probes can be used to screen a human genomic library using appropriately stringent conditions or by PCR. The identification and characterization of human genomic clones is helpful for identifying polymorphisms (including, but not limited to, nucleotide repeats, microsatellite alleles, single nucleotide polymorphisms, or coding single nucleotide polymorphisms), determining the genomic structure of a given locus/allele, and designing diagnostic tests. For example, sequences derived from regions adjacent to the intron/exon boundaries of the human gene can be used to design primers for use in amplification assays to detect mutations within the exons, introns, splice sites (e.g., splice acceptor and/or donor sites), etc., that can be used in diagnostics and pharmacogenomics.

Further, a NHP homolog can be isolated from nucleic acid from an organism of interest by performing PCR using two degenerate or "wobble" oligonucleotide primer pools designed on the basis of amino acid sequences within the NHP products disclosed herein. The template for the reaction may be total RNA, mRNA, and/or cDNA obtained by reverse transcription of mRNA prepared from human or non-human cell lines or tissue known or suspected to express an allele of a NHP gene. The PCR product can be subcloned and sequenced to ensure that the amplified sequences represent the sequence of the desired NHP gene. The PCR fragment can then be used to isolate a full length cDNA clone by a variety of methods. For example, the amplified fragment can be labeled and used to screen a cDNA library, such as a bacteriophage cDNA library. Alternatively, the labeled fragment can be used to isolate genomic clones via the screening of a genomic library.

PCR technology can also be used to isolate full length cDNA sequences. For example, RNA can be isolated, following standard procedures, from an appropriate cellular or tissue source (i.e., one known, or suspected, to express a NHP gene, such as, for example, testis tissue). A reverse transcription (RT) reaction can be performed on the RNA using an oligonucleotide primer specific for the most 5' end of the amplified fragment for the priming of first strand synthesis. The resulting RNA/DNA hybrid may then be "tailed" using a standard terminal transferase reaction, the hybrid may be digested with RNase H, and second strand synthesis may then be primed with a complementary primer. Thus, cDNA sequences upstream of the amplified fragment can be isolated. For a review of cloning strategies that can be used, see e.g., Sambrook et al., 1989, supra.

A cDNA encoding a mutant NHP gene can be isolated, for example, by using PCR. In this case, the first cDNA strand may be synthesized by hybridizing an oligo-dT oligonucleotide to mRNA isolated from tissue known or suspected to be expressed in an individual putatively carrying a mutant NHP allele, and by extending the new strand with reverse transcriptase. The second strand of the cDNA is then synthesized using an oligonucleotide that hybridizes specifically to the 5' end of the normal gene. Using these two primers, the product is then amplified via PCR, optionally cloned into a suitable vector, and subjected to DNA sequence analysis through methods well known to those of skill in the art. By comparing the DNA sequence of the mutant NHP allele to that of a corresponding normal NHP allele, the mutation(s) responsible for the loss or alteration of function of the mutant NHP gene product can be ascertained.

Alternatively, a genomic library can be constructed using DNA obtained from an individual suspected of or known to carry a mutant NHP allele (e.g., a person manifesting a NHP-associated phenotype such as, for example, obesity, high blood pressure, connective tissue disorders, infertility, etc.), or a cDNA library can be constructed using RNA from a tissue known, or suspected, to express a mutant NHP allele. A normal NHP gene, or any suitable fragment thereof, can then be labeled and used as a probe to identify the corresponding mutant NHP allele in such libraries. Clones containing mutant NHP gene sequences can then be purified and subjected to sequence analysis according to methods well known to those skilled in the art.

Additionally, an expression library can be constructed utilizing cDNA synthesized from, for example, RNA isolated from a tissue known, or suspected, to express a mutant NHP allele in an individual suspected of or known to carry such a mutant allele. In this manner, gene products made by the putatively mutant tissue can be expressed and screened using standard antibody screening techniques in conjunction with antibodies raised against normal NHP product, as described below. (For screening techniques, see, for example, Harlow, E. and Lane, eds., 1988, "Antibodies: A Laboratory Manual", Cold Spring Harbor Press, Cold Spring Harbor.)

Additionally, screening can be accomplished by screening with labeled NHP fusion proteins, such as, for example, alkaline phosphatase-NHP or NHP-alkaline phosphatase fusion proteins. In cases where a NHP mutation results in an expressed gene product with altered function (e.g., as a result of a missense or a frameshift mutation), polyclonal antibodies to NHP are likely to cross-react with a corresponding mutant NHP gene product. Library clones detected via their reaction with such labeled antibodies can be purified and subjected to sequence analysis according to methods well known in the art.

The invention also encompasses (a) DNA vectors that contain any of the foregoing NHP coding sequences and/or their complements (i.e., antisense); (b) DNA expression vectors that contain any of the foregoing NHP coding sequences operatively associated with a regulatory element that directs the expression of the coding sequences (for example, baculo virus as described in U.S. Pat. No. 5,869, 336 herein incorporated by reference); (c) genetically engineered host cells that contain any of the foregoing NHP coding sequences operatively associated with a regulatory element that directs the expression of the coding sequences in the host cell; and (d) genetically engineered host cells that express an endogenous NHP gene under the control of an exogenously introduced regulatory element (i.e., gene activation). As used herein, regulatory elements include, but are not limited to, inducible and non-inducible promoters, enhancers, operators and other elements known to those skilled in the art that drive and regulate expression. Such regulatory elements include but are not limited to the human cytomegalovirus (hCMV) immediate early gene, regulatable, viral elements (particularly retroviral LTR promoters), the early or late promoters of SV40 adenovirus, the lac system, the trp system, the TAC system, the TRC system, the major operator and promoter regions of phage lambda, the control regions of fd coat protein, the promoter for 3-phosphoglycerate kinase (PGK), the promoters of acid phosphatase, and the promoters of the yeast α-mating factors.

The present invention also encompasses antibodies and anti-idiotypic antibodies (including Fab fragments), antagonists and agonists of a NHP, as well as compounds or nucleotide constructs that inhibit expression of a NHP gene (transcription factor inhibitors, antisense and ribozyme molecules, or gene or regulatory sequence replacement constructs), or promote the expression of a NHP (e.g., expression constructs in which NHP coding sequences are operatively associated with expression control elements such as promoters, promoter/enhancers, etc.).

The NHPs or NHP peptides, NHP fusion proteins, NHP nucleotide sequences, antibodies, antagonists and agonists can be useful for the detection of mutant NHPs or inappropriately expressed NHPs for the diagnosis of disease. The NHPs or NHP peptides, NHP fusion proteins, NHP nucleotide sequences, host cell expression systems, antibodies, antagonists, agonists and genetically engineered cells and animals can be used for screening for drugs (or high throughput screening of combinatorial libraries) effective in the treatment of the symptomatic or phenotypic manifestations of perturbing the normal function of NHP in the body. The use of engineered host cells and/or animals may offer an advantage in that such systems allow not only for the identification of compounds that bind to the endogenous receptor for a NHP, but can also identify compounds that trigger NHP-mediated activities or pathways.

Finally, the NHP products can be used as therapeutics. For example, soluble derivatives such as NHP peptides/domains corresponding to NHP, NHP fusion protein products (especially NHP-Ig fusion proteins, i.e., fusions of a NHP, or a domain of a NHP, to an IgFc), NHP antibodies and anti-idiotypic antibodies (including Fab fragments), antagonists or agonists (including compounds that modulate or act on downstream targets in a NHP-mediated pathway) can be used to directly treat diseases or disorders. For instance, the administration of an effective amount of soluble NHP, or a NHP-IgFc fusion protein or an anti-idiotypic antibody (or its Fab) that mimics a NHP could activate or effectively antagonize the endogenous NHP receptor. Nucleotide constructs encoding such NHP products can be used to genetically engineer host cells to express such products in vivo; these genetically engineered cells function as "bioreactors" in the body delivering a continuous supply of a NHP, a NHP peptide, or a NHP fusion protein to the body. Nucleotide constructs encoding functional NHP, mutant NHPs, as well as antisense and ribozyme molecules can also be used in "gene therapy" approaches for the modulation of NHP expression. Thus, the invention also encompasses pharmaceutical formulations and methods for treating biological disorders.

Various aspects of the invention are described in greater detail in the subsections below.

5.1 THE NHP SEQUENCES

The cDNA sequences and corresponding deduced amino acid sequences of the described NHPs are presented in the Sequence Listing. SEQ ID NO:7 describes a NHP ORF as well as flanking regions. The NHP nucleotides were obtained from human cDNA libraries using probes and/or primers generated from human gene trapped sequence tags, and genomic sequence. Expression analysis has provided evidence that the described NHP can be expressed a variety of human cells as well as gene trapped human cells.

5.2 NHPs AND NHP POLYPEPTIDES

NHPs, polypeptides, peptide fragments, mutated, truncated, or deleted forms of the NHPs, and/or NHP fusion proteins can be prepared for a variety of uses. These uses include, but are not limited to, the generation of antibodies, as reagents in diagnostic assays, for the identification of other cellular gene products related to a NHP, as reagents in assays for screening for compounds that can be as pharmaceutical reagents useful in the therapeutic treatment of mental, biological, or medical disorders and disease.

The Sequence Listing discloses the amino acid sequences encoded by the described NHP polynucleotides. The NHPs display an initiator methionines in DNA sequence contexts consistent with a translation initiation site, and several of the ORFs display a consensus signal sequence which can indicate that the described NHP ORFs are secreted proteins, or can be membrane associated.

The NHP amino acid sequences of the invention include the amino acid sequences presented in the Sequence Listing as well as analogues and derivatives thereof. Further, corresponding NIP homologues from other species are encompassed by the invention. In fact, any NHPs encoded by a NHP nucleotide sequence described above are within the scope of the invention, as are any novel polynucleotide sequences encoding all or any novel portion of an amino acid sequence presented in the Sequence Listing. The degenerate nature of the genetic code is well known, and, accordingly, each amino acid presented in the Sequence Listing, is generically representative of the well known nucleic acid "triplet" codon, or in many cases codons, that can encode the amino acid. As such, as contemplated herein, the amino acid sequences presented in the Sequence Listing, when taken together with the genetic code (see, for example, Table 4-1 at page 109 of "Molecular Cell Biology", 1986, J. Darnell et al. eds., Scientific American Books, New York, N.Y., herein incorporated by reference) are generically representative of all the various permutations and combinations of nucleic acid sequences that can encode such amino acid sequences.

The invention also encompasses proteins that are functionally equivalent to the NHPs encoded by the presently described nucleotide sequences as judged by any of a number of criteria, including, but not limited to, the ability to bind and cleave a substrate of a NHP, or the ability to effect an identical or complementary downstream pathway, or a change in cellular metabolism (e.g., proteolytic activity, ion flux, tyrosine phosphorylation, etc.). Such functionally equivalent NHP proteins include, but are not limited to, additions or substitutions of amino acid residues within the amino acid sequence encoded by the NHP nucleotide sequences described above, but which result in a silent change, thus producing a functionally equivalent gene product. Amino acid substitutions can be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

A variety of host-expression vector systems can be used to express the NHP nucleotide sequences of the invention. Where, as in the present instance, a NHP peptide or NHP polypeptide is thought to be a soluble or secreted molecule, the peptide or polypeptide can be recovered from the culture media. Such expression systems also encompass engineered host cells that express NHP, or functional equivalent, in situ. Purification or enrichment of a NHP from such expression systems can be accomplished using appropriate detergents and lipid micelles and methods well known to those skilled in the art. However, such engineered host cells themselves may be used in situations where it is important not only to retain the structural and functional characteristics of a NHP, but to assess biological activity, e.g., in drug screening assays.

The expression systems that may be used for purposes of the invention include but are not limited to microorganisms such as bacteria (e.g., *E. coli, B. subtilis*) transformed with recombinant bacteriophage DNA, plasmid DNA or cosmid DNA expression vectors containing NHP nucleotide sequences; yeast (e.g., *Saccharomyces, Pichia*) transformed with recombinant yeast expression vectors containing NHP encoding nucleotide sequences; insect cell systems infected with recombinant virus expression vectors (e.g., baculovirus) containing NHP sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing NHP nucleotide sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the NHP product being expressed. For example, when a large quantity of such a protein is to be produced for the generation of pharmaceutical compositions of and/or containing a NHP, or for raising antibodies to a NHP, vectors that direct the expression of high levels of fusion protein products that are readily purified may be desirable. Such vectors include, but are not limited, to the *E. coli* expression vector pUR278 (Ruther et al., 1983, EMBO J. 2:1791), in which a NHP coding sequence may be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors (Pharmacia or American Type Culture Collection) can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The PGEX vectors are designed to include thrombin or factor Xa protease cleavage sites so that the cloned target gene product can be released from the GST moiety.

In an insect system, *Autographa californica* nuclear polyhidrosis virus (AcNPV) is used as a vector to express foreign. genes. The virus grows in *Spodoptera frugiperda* cells. A NHP coding sequence can be cloned individually into non-essential regions (for example the polyhedrin gene) of the virus and placed under control of an AcNPV promoter (for example the polyhedrin promoter). Successful insertion of NHP coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted sequence is expressed (e.g., see Smith et al., 1983, J. Virol. 46: 584; Smith, U.S. Pat. No. 4,215,051).

In mammalian host cells, a number of viral-based expression systems may be utilized. In cases where an adenovirus is used as an expression vector, the NHP nucleotide sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing a NHP product in infected hosts (e.g., See Logan & Shenk, 1984, Proc. Natl. Acad. Sci. USA 81:3655–3659). Specific initiation signals may also be required for efficient translation of inserted NHP nucleotide sequences. These signals include the ATG initiation codon and adjacent sequences. In cases where an entire NHP sequence or cDNA, including its own initiation codon and adjacent sequences, is inserted into the appropriate expression vector, no additional translational control signals may be needed. However, in cases where only a portion of a NHP coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (See Bittner et al., 1987, Methods in Enzymol. 153:516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include, but are not limited to, CHO, VERO, BHK, HeLa, COS, MDCK, 293, 3T3, WI38, and in particular, human cell lines.

For long-term, high-yield production of recombinant proteins, stable expression is preferred. For example, cell lines which stably express the NHP sequences described above can be engineered. Rather than using expression vectors which contain viral origins of replication, host cells can be transformed with DNA controlled by appropriate expression control elements (e.g., promoter, enhancer sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express a NHP product. Such engineered cell lines may be particularly useful in screening and evaluation of compounds that affect the endogenous activity of a NHP product.

A number of selection systems may be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy, et al., 1980, Cell 22:817) genes can be employed in tk⁻, hgprt⁻ or aprt⁻ cells, respectively. Also, antimetabolite resistance can be used as the basis of selection for the following genes: dhfr, which confers resistance to methotrexate (Wigler, et al., 1980, Natl. Acad. Sci. USA 77:3567; O'Hare, et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147).

Alternatively, any fusion protein can be readily purified by utilizing an antibody specific for the fusion protein being expressed. For example, a system described by Janknecht et al. allows for the ready purification of non-denatured fusion proteins expressed in human cell lines (Janknecht, et al., 1991, Proc. Natl. Acad. Sci. USA 88:8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$. nitriloacetic acid-agarose columns and histidine-tagged proteins are selectively eluted with imidazole-containing buffers.

5.3 ANTIBODIES TO NHP PRODUCTS

Antibodies that specifically recognize one or more epitopes of a NHP, or epitopes of conserved variants of a NHP, or peptide fragments of a NHP are also encompassed by the invention. Such antibodies include but are not limited to polyclonal antibodies, monoclonal antibodies (mAbs), humanized or chimeric antibodies, single chain antibodies, Fab fragments, F(ab')₂ fragments, fragments produced by a Fab expression library, anti-idiotypic (anti-Id) antibodies, and epitope-binding fragments of any of the above.

The antibodies of the invention may be used, for example, in the detection of a NHP in a biological sample and may, therefore, be utilized as part of a diagnostic or prognostic technique whereby patients may be tested for abnormal amounts of, NHP. Such antibodies may also be utilized in conjunction with, for example, compound screening schemes for the evaluation of the effect of test compounds on expression and/or activity of a NHP sequence product. Additionally, such antibodies can be used in conjunction gene therapy to, for example, evaluate the normal and/or engineered NHP-expressing cells prior to their introduction into the patient. Such antibodies may additionally be used as a method for the inhibition of abnormal NHP activity. Thus, such antibodies may, therefore, be utilized as part of treatment methods.

For the production of antibodies, various host animals may be immunized by injection with a NHP, an NHP peptide (e.g., one corresponding to a functional domain of a NHP), truncated NHP polypeptides (NHP in which one or more domains have been deleted), functional equivalents of a NHP or mutated variants of a NHP. Such host animals may include but are not limited to pigs, rabbits, mice, goats, and rats, to name but a few. Various adjuvants may be used to increase the immunological response, depending on the host species, including but not limited to Freund's adjuvant (complete and incomplete), mineral salts such as aluminum hydroxide or aluminum phosphate, surface active substances such as lysolecithin, pluronic polyols, polyanions, peptides, oil emulsions, and potentially useful human adjuvants such as BCG (bacille Calmette-Guerin) and *Corynebacterium parvum*. Alternatively, the immune response could be enhanced by combination and or coupling with molecules such as keyhole limpet hemocyanin, tetanus toxoid, diptheria toxoid, ovalbumin, cholera toxin or fragments thereof. Polyclonal antibodies are heterogeneous populations of antibody molecules derived from the sera of the immunized animals.

Monoclonal antibodies, which are homogeneous populations of antibodies to a particular antigen, can be obtained by any technique which provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine ₁₁A and a human immunoglobulin constant region. Such technologies are described in U.S. Pat. Nos. 6,075,181 and 5,877,397 and their respective disclosures which are herein incorporated by reference in their entirety.

Alternatively, techniques described for the production of single chain antibodies (U.S. Pat. No. 4,946,778; Bird, 1988, Science 242:423–426; Huston et al., 1988, Proc. Natl. Acad. Sci. USA 85:5879–5883; and Ward et al., 1989, Nature 334:544–546) can be adapted to produce single chain antibodies against NHP sequence products. Single chain antibodies are formed by linking the heavy and light chain fragments of the Fv region via an amino acid bridge, resulting in a single chain polypeptide.

Antibody fragments which recognize specific epitopes may be generated by known techniques. For example, such fragments include, but are not limited to: the F(ab')₂ fragments which can be produced by pepsin digestion of the antibody molecule and the Fab fragments which can be generated by reducing the disulfide bridges of the F(ab')₂ fragments. Alternatively, Fab expression libraries may be constructed (Huse et al., 1989, Science, 246:1275–1281) to allow rapid and easy identification of monoclonal Fab fragments with the desired specificity.

Antibodies to a NHP can, in turn, be utilized to generate anti-idiotype antibodies that "mimic" a given NHP, using techniques well known to those skilled in the art. (See, e.g., Greenspan & Bona, 1993, FASEB J 7(5):437–444; and Nissinoff, 1991, J. Immunol. 147(8):2429–2438). For example antibodies which bind to a NHP domain and competitively inhibit the binding of NHP to its cognate receptor can be used to generate anti-idiotypes that "mimic"

a NHP and, therefore, bind and activate or neutralize a receptor. Such anti-idiotypic antibodies or Fab fragments of such anti-idiotypes can be used in therapeutic regimens involving a NHP signaling pathway.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description. Such modifications are intended to fall within the scope of the appended claims. All cited publications, patents, and patent applications are herein incorporated by reference in their entirety.

What is claimed is:

1. An isolated nucleic acid molecule comprising the nucleotide sequence of SEQ ID NO: 3.

2. An isolated nucleic acid molecule comprising a nucleotide sequence that:

(a) encodes the amino acid sequence set forth in SEQ ID NO: 4; and (b) hybridizes under highly stringent conditions to the complement of the nucleotide sequence of SEQ ID NO: 3.

3. An isolated nucleic acid molecule according to claim 1, wherein said nucleotide sequence is a cDNA.

4. An expression vector comprising a nucleic acid sequence of claim 2.

5. A cell comprising the expression vector of claim 4.

* * * * *